United States Patent [19]

Benzies

[11] Patent Number: 4,573,984

[45] Date of Patent: Mar. 4, 1986

[54] WASTE RETAINING RECEPTACLES FOR PATIENTS WITH COLOSTOMIES AND ILEOSTOMIES

[76] Inventor: George Y. Benzies, 47, The Riding, Woking, Surrey, England, GU215TA

[21] Appl. No.: 532,711

[22] Filed: Sep. 14, 1983

[30] Foreign Application Priority Data

Dec. 11, 1982 [GB] United Kingdom ............... 8235367

[51] Int. Cl.$^4$ ............................................. A61F 5/44
[52] U.S. Cl. ................................................ 604/339
[58] Field of Search .................. 604/318, 332–345, 604/369; 128/767, 771; 340/618

[56] References Cited

U.S. PATENT DOCUMENTS

| | | | |
|---|---|---|---|
| 3,769,497 | 10/1973 | Frank | 128/771 |
| 3,898,990 | 8/1975 | Nolan | 604/336 |
| 3,902,496 | 9/1975 | Eakin | 604/334 |
| 3,908,658 | 9/1975 | Marsan | 604/336 |
| 4,343,316 | 8/1982 | Jespersen | 128/767 |
| 4,475,908 | 10/1984 | Lloyd | 604/339 |

OTHER PUBLICATIONS

"Gore-Tex", Catalog Cut, W. L. Gore & Assoc., Inc., Elkton, Maryland, 1980.

Primary Examiner—J. L. Kruter
Attorney, Agent, or Firm—Fulwider, Patton, Rieber, Lee & Utecht

[57] ABSTRACT

A waste retaining bag 10 for sealingly adhering to the body of a user around a stoma through which body waste issues includes an inlet 11 for waste and a seal arrangement which comprises two laminae 13, 15, bonded one to each side of a relatively thick resiliently deformable ring 14. Lamina 13 is attached to the bag adjacent the inlet 11 and lamina 15 is provided with an adhesive coating for adhering to the body of a user.

8 Claims, 4 Drawing Figures

WASTE RETAINING RECEPTACLES FOR PATIENTS WITH COLOSTOMIES AND ILEOSTOMIES

BACKGROUND OF THE INVENTION

1. Field of the Invention

This invention relates to waste retaining receptacles for adhering to the body of a user around a stoma, fistula or similar orifice to collect body waste issuing from the user's body.

By way of example, reference is made to the urostomy type of surgical operation and specifically to Ileal conduit appliances. An Ileal conduit operation may be performed for one of a number of reasons; for example, when a non-invasive carcinoma is present in the bladder or when a person is continuously incontinent. The operation consists essentially of a cystectomy (the total removal of the bladder) and the grafting of the two ureter tubes from the kidneys to a section of the small bowel which leads to a stoma exit normally located at one side of the torso. By contrast, in a colostomy operation an end section of the bowel is caused to exit a stoma more centrally situated on the stomach.

2. Description of the Prior Art

In the past, it has been customary to fit a plastic bag over the stoma interspaced with a sheet of intermediate material which is intended to seal the bag to the user's body by adhering to the skin around the stoma. In use, urine or other body waste which is being continuously discharged from the stoma, collects in the plastic bag. In practice, it is found that this form of bag does not provide a reliable seal between the user's body and thus allows prolonged contact of the skin with body waste fluid which causes irritation causing a sore, excoriation or a similar skin condition. This is unpleasant for the user and also makes it difficult to seal a subsequent bag to the stoma because of the roughness or degradation of the surface of the irritated skin.

An attempt has been made to overcome this problem by providing the bag with a sealing arrangement in the form of an 'O' ring which fits around the base of the stoma located within a rigid or semi-rigid face plate, the bag being strapped around the waist of a user by means of straps secured at their ends to the face plate. This arrangement is cumbersome in view of the straps and the rigidity of the face plate for the 'O' ring seal. In addition, experience has shown that the stoma is often a very sensitive area and the fitting of the 'O' ring over the stoma can be very painful.

OBJECTS OF THE INVENTION

Accordingly, it is one object of this invention to provide a waste retaining bag for collecting waste issuing from a user's body via a stoma or similar orifice which provides a fluid-tight seal between the bag and the user's body.

It is a further object of this invention to provide a waste retaining bag which may be attached to a user's body without the need for straps etc.

It is a still further object of this invention to provide a bag in which a visual indication of the state of the seal is given.

It is a still further object to provide a bag which does not collapse on emptying.

SUMMARY OF THE INVENTION

With the foregoing and other objects in view, a waste retaining bag in accordance with certain aspects of the invention includes an inlet aperture for waste, seal means surrounding said aperture for sealingly being adhered to a user's body around a stoma, said seal means comprising spaced laminae of relatively thin material bonded one to each side of a relatively thick but flexible sheet, one of the laminae being attached to the bag, the other being adapted for bonding to the user's body around the stoma.

Other objects, advantages, and features of the invention will be apparent from the following description of a specific embodiment when read in conjunction with the appended drawings.

DETAILED DESCRIPTION OF THE DRAWINGS

Figure 1:
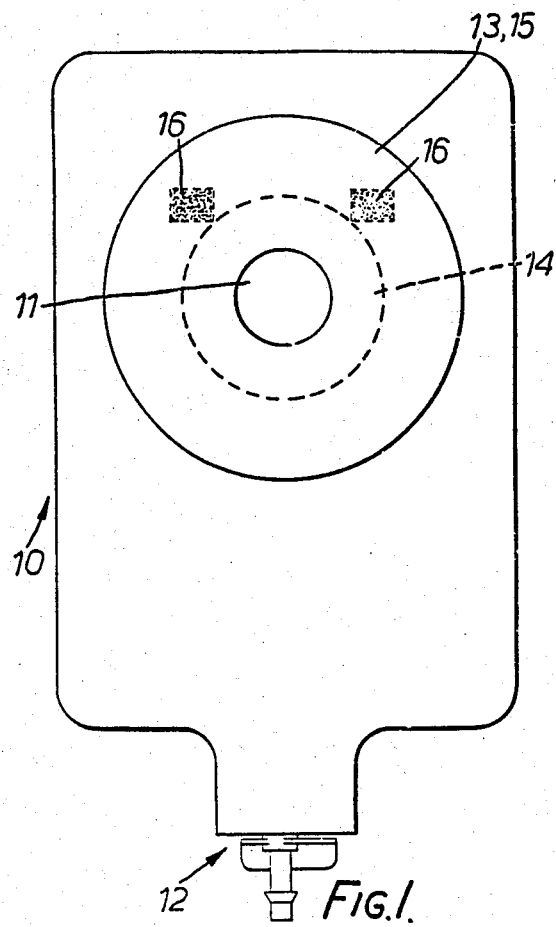
FIG. 1 is a plan view of a waste retaining bag in accordance with one specific embodiment of the invention.
Figure 2:
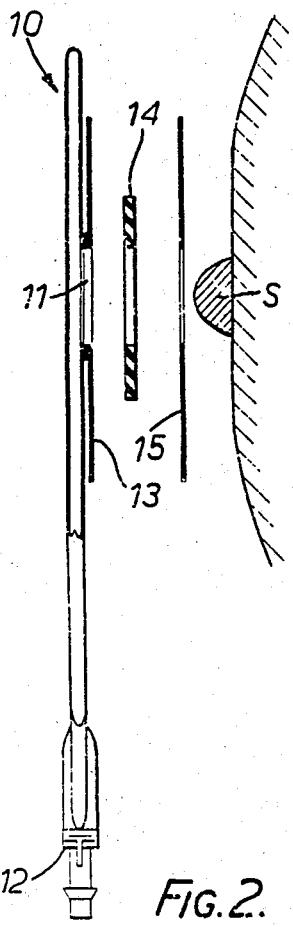
FIG. 2 is an exploded view in cross-section of the bag of FIG. 1, also showing the stoma of a user.
Figure 3:
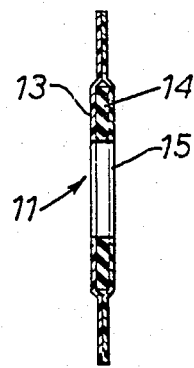
FIG. 3 is a section view, on an enlarged scale, of the sealing arrangement of the bag of FIGS. 1 and 2.

Referring initially to FIGS. 1 to 3, the bag 10 is formed of a flexible impervious sheet material such as plastics or rubber having an inlet 11 for body waste formed in an upper region of the bag and a drain tap provided at its lower end for allowing fluid or body waste which collects in the bag to be drained.

In its collapsed or empty state (as shown in FIG. 2) the bag 10 is generally flat, so that it may conform to the shape of the user's body. The bag may incorporate a non-return arrangement (not shown, but the design of which is believed to be within the competence of one skilled in the art) which, when the bag is attached to a user, prevents fluid collected in the lower portion of the bag from returning to the inlet.

A square-shaped lamina 13 of material (for example Micropore sheet manufactured by Minnesota Mining and Manufacturing Company, St. Paul, Minnesota), having one surface coated with an adhesive and having an aperture matching that of the inlet 11 of the bag, is secured around the inlet of the bag with its non-adhesive coated surface facing the adjacent sheet member of the bag. The lamina 13 may be attached directed to the bag material surrounding the aperture or it may be attached thereto by means of an intermediary annulus of material which, itself, is secured around the periphery of inlet 11 by heat welding or another suitable process The form of bag so far described is manufactured and marketed by Hollister Incorporated, Libertyville, Illinois, under the description Hollister Lo-profile bag.

A ring 14 of rubber or similar material being relatively resiliently deformable and thick compared to lamina 13, and having an adhesive coated surface and an opposed non-adhesive coated surface (for example a 'Comfeel' ring manufactured by Coloplast A/S, Espergaerde, Denmark) is superimposed on lamina 13 with its non-adhesive coated surface being placed in contact with the adhesive coated surface of lamina 13 to bond it thereto.

A further lamina 15 of material having an aperture generally matching those of the inlet of the bag and the ring 14 and having each of its opposed surfaces coated with adhesive (for example, a Stomaseal adhesive disc manufactured by Minnesota Mining and Manufacturing Co., U.S.A.) is laid over ring 14 and that exposed peripheral part of lamina 13 extending beyond the ring 14 so as to form a composite structure in which a relatively thick and resiliently deformable core is sandwiched by two laminae (albeit of different material).

The exposed adhesive surface of the laminae 15 remote from the bag is preferably covered with a release sheet to protect the adhesive coating until such time as it is wished to adhere the bag around the stomas or similar orifice.

In order to prevent the bag 10 from collapsing in a wrinkled form when it is drained, the surface of the lamina 13 adjacent an upper end region of the bag 10 is secured to the bag by means of one or more strips 16 of double sided adhesive material or other suitable means. This effectively supports the bag at an upper extremity so that the bag may drain without folding over, or wrinkling near the inlet 11.

Figure 4:
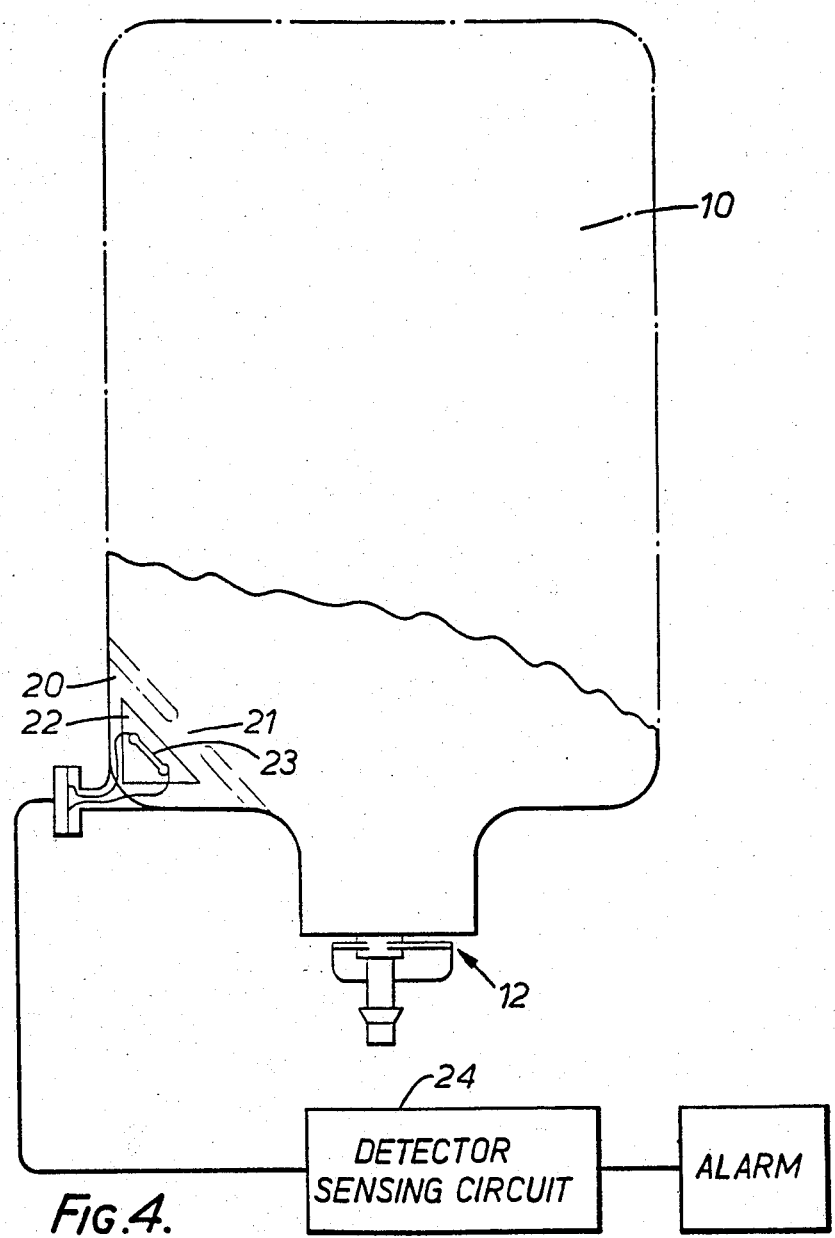
FIG. 4 is a detail view of a warning device for indicating that the bag of FIGS. 1 to 3 is full.

Referring to FIG. 4, there is illustrated a form of warning arrangement for alerting the user of the bag to the fact that the bag is nearly full. In this arrangement, a lower corner region of the bag is formed, by heat welding or other suitable means, so as to define a small enclosure 20 for fluid which communicates with the remainder of the bag through passage 21. As the bag fills with fluid, the fluid also passes into enclosure 20. As the bag fills up, the hydrostatic pressure in enclosure 20 will increase thereby tending to stretch the material forming the enclosure. The enclosure is coated with a brittle plastics coating 22 on which is formed a conductive track 23. The bag is provided with a terminal which connects the conductive track 23 to a sensing circuit 24. The thickness and fracture qualities of the coating 22 are selected so that as the bag nears a full condition, the hydrostatic pressure generated in the enclosure 20 stretches the material of the enclosure sufficiently to cause coating 22 to crack, thereby to break the detection circuit and hence to cause an alarm to be actuated in the form of a buzzer or the like.

Instead of the just-described form of warning arrangement, other forms may be used, for example those using sensors which detect gas volume/liquid volume or specific gas generation along the lines of flueric gas sensors.

In use, the area surrounding the area around stoma is cleaned to remove oil, hair, lint etc., thus to provide an adhesive receptive skin surface. The aperture of the inlet 11 of the bag 10 is selected to be slightly larger than the stoma. The release sheet is removed from the lamina 15 and the bag is positioned with the inlet 11 located over the stoma and then pressed against the body to cause the lamina 15, and thus the bag itself, to be adhered to the body of the user. After a period of use of the bag, if the material of the bag and the lamina 13 are translucent, the user will notice that a "tide mark" has formed in the ring 14. This tide mark indicates the extent to which the body fluid has penetrated the ring 14. When the tide mark has reached the outer edge of ring 14, then it is necessary to remove the bag and replace it by another. However, the user may empty the bag as often as is necessary using the drain tap.

Tests have shown that the useful life of the bag just described before the seal between the body and the bag is degraded is up to three times the life of the Hollister bag previously described.

The Applicant postulates that the reasons for the considerably extended life of the bag of this invention include the fact that the composite nature of the seal (lamina 13 and lamina 15 to enter side of ring 14) provides a structure in which the peripheral bonding of lamina 13 to lamina 15 gives greater strength to the aperture. The location of two laminae to either side of ring 14, which acts as a spacer, gives strength which allows resiliently restrained flexure of the seal as it conforms to body movement of the user and also allows deformation of the ring 14 in the direction of its thickness to accommodate the surface characteristics of the underlying skin, thus preventing the formation of wrinkles in the seal surface which would allow seepage of fluid.

It is also found that the area on the skin around the stoma to which the seal is adhered may be less than that required by previous forms of bag since the ring 14 may be of smaller diameter than the corresponding bonding item of the previous forms of bag.

This described arrangement does not require any uncomfortable rigid plastic pieces or a belt to retain the bag in position. It has the feature that, by suitable selection of materials, the state of the seal may be assessed by observing the tide mark caused by progressive penetration of body fluid into ring 14. The bag 10 is also prevented from collapsing by the securing of an upper part of the bag to a part of the seal which, in turn, is bonded to the user's body.

As described above, the bag includes an alarm arrangement which allows the user to use the bag whilst asleep without fear of overfilling the bag. Previous attempts to solve this problem have led to the use of extension tubes which work on the inherently false principle that the patient will remain in one position throughout the night. Problems also arise since, unless very special precautions are taken, a vacuum is formed in the bag as it is emptying and this can cause the bag to wrinkle, leading to a no-flow situation.

The bag and seal should naturally be formed of hypoallergic material to avoid skin rashes etc., and the face of the bag which in use contacts the abdomen of the user is preferably flocked so as to reduce sweating.

The material from which the bag itself is formed may be a plastics material or rubber material. The Applicant has found that the body wastes may react adversely with the plasticizer employed in various plastics sheet materials, and for this reason, polybutylene is proposed as a suitable material for the bag.

The laminae are typically each about 0.001 to 0.002 inches in thickness and the ring is typically about 0.050 inches in thickness.

In the specific arrangement described and illustrated ring 14 is formed of material having the deformation characteristics of rubber. This material can be a solid foam rubber like material. As an alternative however the ring may be formed of porous material adapted to allow passage of air but to prevent substantial egress of liquid. Such material is manufactured by the Minnesota Mining and Manufacturing Company under the description "Micropore foam".

I claim:

1. A waste retaining receptacle for adhering to the body of a user to collect body waste issuing from the user's body via a stoma or similar orifice, said receptacle including an inlet aperture for waste, seal means surrounding said aperture for sealingly being adhered to the user's body around the stoma, said seal means comprising two laminae of relatively thin material bonded one to each side of a flexible annular ring resiliently deformable non-viscous material having a thickness substantially greater than the thickness of said laminae, one of the laminae being attached to the receptacle around said inlet aperture, and the other lamina being adapted to be adhered to the user's body around the stoma, said laminae extending each a substantial distance beyond the periphery of said flexible ring and bonded to one another over a substantial surface area at least around a major portion of the periphery of said flexible ring sheet.

2. A waste retaining receptacle as recited in claim 1, wherein said flexible ring is formed of material having the deformation characteristics of rubber.

3. A waste retaining receptacle as recited in claim 1, wherein said flexible material is a foam material.

4. A waste retaining receptacle as recited in claim 2, wherein said flexible material is a foam material.

5. A waste retaining receptacle as recited in claim 1, wherein said flexible material is a porous material adapted to allow passage of air but to prevent egress of liquid.

6. A waste retaining receptacle as recited in claim 1, which further includes sensor means adapted to indicate when the receptacle approaches a full condition.

7. A waste retaining bag for adhering to the body of a user to collect body waste issuing from a stoma or similar orifice, said bag including first and second sheet members sealingly attached together around their peripheries to provide a fluid reservoir, one of said sheet members including an aperture defining an inlet for body waste, said inlet including a seal arrangement comprising a first lamina having an aperture generally matching that of the inlet and being secured to said inlet, a second lamina adapted for adhering to the body of a user, and a relatively resiliently deformable annular ring interposed between said laminae and having a thickness substantially greater than the thickness of said laminae, said first and second laminae extending each a substantial distance beyond the periphery of said ring and bonded to one another over a substantial surface area at least around a major portion of the periphery of said ring.

8. A waste retaining bag as recited in claim 7 wherein the inlet is provided in the upper portion of said one sheet member and said first lamina is attached to a region of said one sheet member adjacent the upper end region thereof.

* * * * *